United States Patent [19]

Imahashi et al.

[11] Patent Number: 4,844,611
[45] Date of Patent: Jul. 4, 1989

[54] SPLIT STREAM FLOW CELL

[75] Inventors: Toru Imahashi, Hachioji; Naoyuki Maruyama, Fussa; Hideki Konishi; Muneo Saito, both of Hachioji, all of Japan

[73] Assignee: Nihon Bunko Kogyo Kabushiki Kaisha, Hachioji, Japan

[21] Appl. No.: 203,444

[22] Filed: Jun. 3, 1988

[30] Foreign Application Priority Data

Jun. 5, 1987 [JP] Japan ................... 62-141020

[51] Int. Cl.⁴ .................................. G01N 21/05
[52] U.S. Cl. ..................... 356/246; 250/373; 356/410
[58] Field of Search ............... 356/246, 410, 411, 440; 250/373, 576

[56] References Cited

U.S. PATENT DOCUMENTS

| 3,614,452 | 1/1969 | Felton | 356/410 X |
|---|---|---|---|
| 4,019,372 | 4/1977 | Parkell et al. | 250/576 X |
| 4,260,258 | 4/1981 | Rose et al. | 250/573 X |
| 4,276,475 | 6/1981 | Nelson | 250/373 |
| 4,501,969 | 2/1985 | Lymneos | 250/373 |

FOREIGN PATENT DOCUMENTS 54-33871 10/1979 Japan .

Primary Examiner—Vincent P. McGraw
Attorney, Agent, or Firm—Browdy and Neimark

[57] ABSTRACT

The present invention relates to a split stream flow cell which is used for a UV detector of liquid chromatography and in which a UV light for detecting absorption of the light is transmitted through a sample solution flowing in the cell. It is an object of the present invention to reduce the influences of both the flow effect and the liquid lens effect without cell volume being made too large. To this end, a split stream flow cell of the present invention comprises a split flow channel (12) which passes through a cell block (10) and which has a central portion communicating with an inlet channel (18), both ends communicating with an outlet channel (38), and both sides symmetrical with respect to the central portion, the diameter thereof being increased from a given position in the central portion toward both ends.

11 Claims, 5 Drawing Sheets

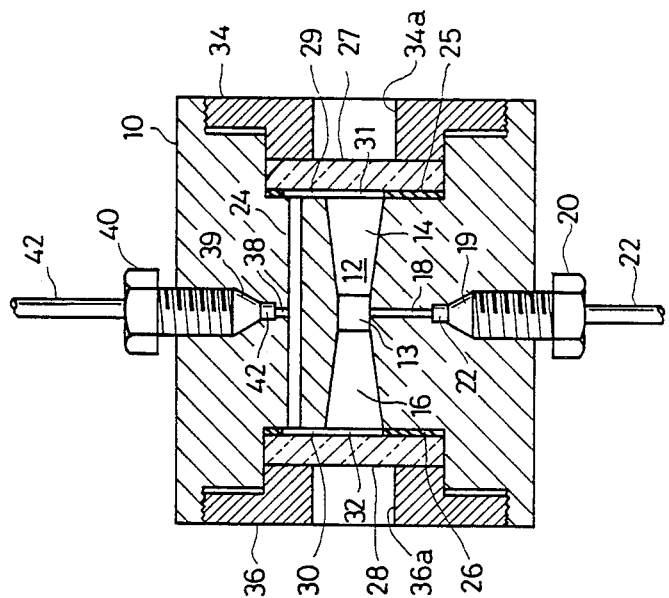
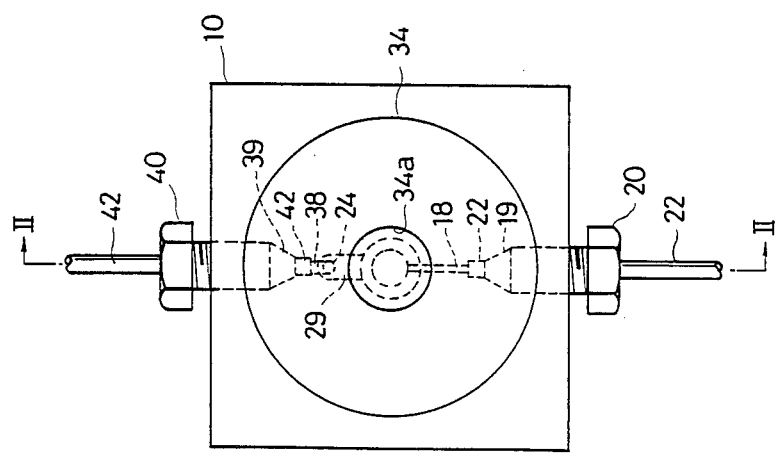
FIG. 1
FIG. 2

SPLIT STREAM FLOW CELL

BACKGROUND OF THE INVENTION

1. Field of the Invention

The present invention relates to a split stream flow cell which is used in a UV detector for liquid chromatography and in which light for detecting the absorption of light is transmitted through a sample solution in the cell.

2. Description of the Prior Art

A method of reducing the measurement time in liquid chromatography is one in which the flow of an eluate is changed with the passage of time.

However, since the base line of the output from a UV detector is changed by the flow (referred to as "flow effect" hereinafter), the detected value is incorrect.

Therefore, a split stream flow cell has been proposed as a means for solving the above-described problem (U.S. Pat. No. 3,614,452). This split stream flow cell has an arrangement in which an inlet channel communicates with the center of a split flow channel passing through a cell block, an outlet channel communicates with both ends of the split flow channel, and openings at both ends of the split flow channel are closed by window members. Since the eluate from a column is passed through divided portions from the center of the split flow channel to the ends thereof, the influence of the flow upon the light transmitting through the cell is reduced, resulting in a reduction to the extent to which the above-described base line changes.

Another method of reducing the measurement time is a gradient elution method in which the components of an eluate is changed with the passage of time.

However, if the components of the eluate is changed, since the known liquid lens effect causes light to be refracted and thus absorbed by the wall surface of the split flow channel, or the divergent light to be bent toward a photodetector element, the energy of light reaching the photodetector element is reduced or increased, with the base line of UV-detection thereby being changed.

A tapered cell is well known as a flow cell which reduces the liquid lens effect in openings at the ends of a tapered hole passing through a cell block (Japanese Patent Publication No. 33871/1979, U.S. Pat. Ser. No. 470,076). In order to reduce the liquid lens effect, it is necessary to increase the inclination of the inner wall of a cell with respect to the center thereof.

However, if the degree of inclination is large, the volume of the cell becomes too large, resulting in peak broadening or re-mixing of the components of a sample.

There is no flow cell in which the influences of the flow effect and the liquid lens effect are both reduced, and a proposal for such a flow cell has been awaited for a long time.

SUMMARY OF THE INVENTION

It is an object of the present invention to provide a split stream flow cell which can adequately reduce the influences of both the flow effect and the liquid lens effect without the cell volume being made too large.

To achieve this end, a split stream flow cell to which the present invention relates comprises a cell block, a split flow channel passing through the cell block, an inlet channel communicating with the center of the split flow channel, an outlet channel communicating with the ends of the split flow channel, and transparent window members which serve to close openings at the ends of the split flow channel, the split flow cell being characterized in that both sides of the split flow channel are symmetrical with respect to a central portion and the diameter of the split flow channel is increased from a given position in the central portion thereof toward its ends.

Since the diameter of the split flow channel is increased from a given position at a central portion thereof toward either ends, the present invention has an excellent effect in that the influence of the flow effect and the liquid lens effect can both be sufficiently reduced.

BRIEF DESCRIPTION OF THE DRAWINGS

FIG. 1 is a front view of a split stream flow cell of a first embodiment;

FIG. 2 is a sectional view taken along the line II—II of FIG. 1;

FIG. 7 is a block diagram of a testing device;

FIG. 8 is a graph of the changes with time in the composition ratio of a mobile phase;

FIG. 9 is a graph of the changes in the base line of the output from a UV detector in tests on the split stream flow cell shown in FIG. 2 and a conventional tapered cell under the conditions shown in FIG. 8;

FIG. 10 is a graph of the changes with time in the flow of a mobile phase;

FIG. 11 is a graph of the changes in the base line of the output from the UV detector in tests performed on the split stream flow cell and the tapered cell under the conditions shown in FIG. 10; and FIG. 12 is a graph corresponding to FIG. 9 when the diameter of an inlet channel of the split stream flow cell is increased.

DETAILED DESCRIPTION OF PREFERRED EMBODIMENT

Figure 4:
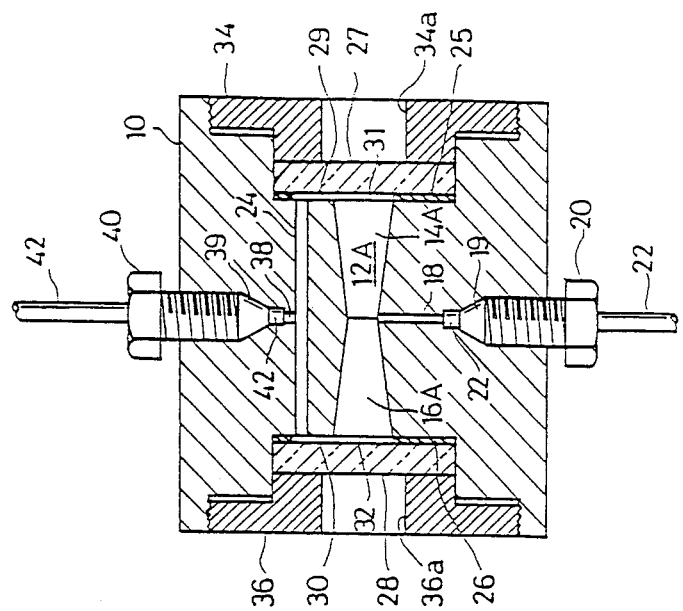
FIG. 4 is a sectional view taken along the line IV—IV of FIG. 3.

Embodiments of the present invention are described below with reference to the drawings.

FIG. 1 is a front view of a split stream flow cell of a first embodiment, and FIG. 2 is a sectional view taken along the line II—II of FIG. 1.

The split stream flow cell is symmetrical with respect to a plane which passes through the vertical axis of the cell in FIG. 1 or 2, perpendicular to the paper.

A cell block 10 is made of a PTFE (polytetrafluoroethylene) resin or stainless steel, and a split flow channel 12 passes through the cell block 10. This split flow channel 12 has rotational symmetry with respect to the axis thereof, and comprises a cylindrical portion 13 and truncated cone portions 14, 16 which each have a diameter increasing toward the ends of the split flow channel 12.

The volume of the split flow channel 12 is preferably as small as possible in order to prevent re-mixing of a sample which has been separated into components, and peak broadening. However, if the axial length of the split flow channel 12 is too small, the light energy absorbed by the sample solution passing through the split flow channel 12 is undesirably reduced.

An inlet channel 18 which is perpendicular to the inner wall of the split passage 12 is caused to communicate with the center of the split flow channel 12. The end of an inlet pipe 22 is passed through central holes of a ferrule 19 and a joint 20, and the joint 20 is screwed into the cell block 10 so that the end of the ferrule 19 bites into the inlet pipe 22, the inlet channel 18 thereby being connected to the inlet pipe 22.

A confluent channel 24 parallel to the axis of the split flow channel is also passed through the cell block 10. Openings at both ends of the confluent channel 24 and the split flow channel 12 are respectively closed by circular window plates 27, 28 with packings 25, 26 therebetween. The packings 25, 26 are each made of a fluorine resin and have holes 31, 32 which are bored therethrough to correspond to the openings at both ends of the split flow channel 12, the confluent channel 24, communicating channels 29, 30, respectively. These communicating channels 29, 30 are formed by the end surfaces of the cell block 10, the packings 25, 26, and the window plates 27, 28, respectively. The split flow channel 12 and the confluent channel 24 are caused to communicate with each other by the communicating channels 29, 30.

The window plates 27, 28 are each formed of a material through which light is transmitted, such as a silica glass or sapphire. The window plates 27, 28 are fixed to the cell block 10 by screwing window pressers 34, 36, respectively, into the cell block 10. The window pressers 34, 36 are each made of, for example, brass or stainless steel. The window pressers 34, 36 have transmission holes 34a, 36a, respectively, which are bored to correspond to the openings at both ends of the split flow channel 12.

An outlet channel 38 is caused to communicate with the center of the confluent channel 24, perpendicular to the confluent channel 24. The base end of an outlet pipe 42 is passed through central holes of a ferrule 39 and a joint 40, and the joint 40 is screwed into the cell block 10 so that the end of the ferrule 39 bites into the outlet pipe 42, the outlet channel 38 thereby being connected to the outlet pipe 42.

In FIG. 2, the strength of light transmitted through the window plate 28, the sample solution in the split flow channel 12, and the window plate 27 is detected by a photodetector element (not shown) which is disposed near the window plate 27.

In the above-described configuration, the sample solution flows into the center of the split flow channel 12 from the inlet channel 18, and is divided into flows which pass through the truncated cone portions 14, 16, pass through the communicating channels 29, 30, respectively, flow into the confluent channel 24 in which the flows are combined, then flow out from the outlet channel 28.

The diameter of the inlet channel 18 is much smaller than that of the central portion of the split flow channel 12. For example, the diameter of the cylindrical portion 13 is 0.7 mm, while the diameter of the inlet channel 18 is 0.25 mm. Therefore, the flow rate of the sample solution flowing in the cylindrical portion 13 is sufficiently greater than that of the sample solution within the cylindrical portion 13, so that the sample solution flowing into the cylindrical portion 13 collides with the inner wall of the cylindrical portion 13, producing fluid mixing. Thus, since the distribution of flow rates at the two end surfaces of the cylindrical portion 13 is made uniform, the liquid lens effect produced at the center of the split flow channel 12 becomes negligible. Therefore, the cylindrical portion need not be tapered, enabling the truncated cone portions 14, 16 to be greatly tapered.

When the sample solution is some distance from the central portion of the split flow channel 12, the flow of the sample solution approaches laminar flow and tends to have a distribution of flow rates in the form of a paraboloid of revolution. However, since the diameter of the split flow channel 12 increases toward both ends thereof, any increase in the flow rate in the portion close to the center of the split flow channel 12 is controlled. Therefore, the liquid lens effect produced in the truncated cone portions 14, 16 is small.

In addition, since the axial length of each of the truncated cone portions 14, 16 is half or less of the axial length of the tapered cell disclosed in Japanese Patent Publication No. 33871/1979, the truncated cone portions can be greatly tapered without their volumes becoming too large. The liquid lens effect can be therefore reduced to less than that produced in the conventional tapered cell.

A comparison to the conventional tapered cell is made below, using an example of numerical values of the dimensions of the split stream flow cell shown in FIGS. 1 and 2.

The split flow channel 12 has an axial length of 9.4 mm and the diameter of each of the openings at its ends is 1.4 mm. The cylindrical portion 13 of the split flow channel 12 has an axial length of 1.0 mm and a diameter of 0.7 mm.

In this example, the inclination of the inner wall of the truncated cone portion 14 is 5.4° with respect to the axis of the split flow channel 12, and the volume of the cell is 9.9 l.

On the other hand, if, in the tapered cell with which the example is compared, the diameter of an opening on a small-diameter side is 0.7 mm, the inclination of the inner wall of the cell with respect to the axis thereof is 5.4°, and the axial length is 9.4 mm, the cell volume is 34.5 l. In other words, the volume of the split stream flow cell is 1/3.5 of the volume of the tapered cell.

In the tapered cell, if the diameter of the opening at one end thereof is 0.7 mm, the diameter of the opening at the other end is 1.4 mm, and the axial length is 9.4 mm, the inclination of the inner wall of the cell with respect to the axis thereof is 2.13°, which is 1/2.5 of that of the split stream flow cell.

In this tapered cell, the taper angle is smaller than the desired angle (3.0-6.0 degrees of so), although the volume of the cell is decreased. According to the invention, it is possible to obtain desired taper angle of the truncated cone portions 14, 16, while reducing the volume of the cell.

A description will now be made of the flow effect. Although there is no fixed theory with respect to the cause of the flow effect, it is thought that the effect is mainly caused by non-uniformity in the distribution of flow rates.

Since the sample solution flowing into the cylindrical portion 13 from the inlet channel 18 is divided into flows that pass respectively through the truncated cone portions 16, 16, its flow rate is reduced to half that of the case in which the sample solution passes through only one channel. Therefore, the distribution of flow rates is made more uniform, and thus the flow effect is reduced.

It is described in U.S. Pat. No. 3,614,452 that since the sample solution is divided into flows passing in opposite directions, the relationships of these flows to the direction of propagation of light are opposite to each other, so that the flow effects are offset and are thus reduced.

Figure 3:
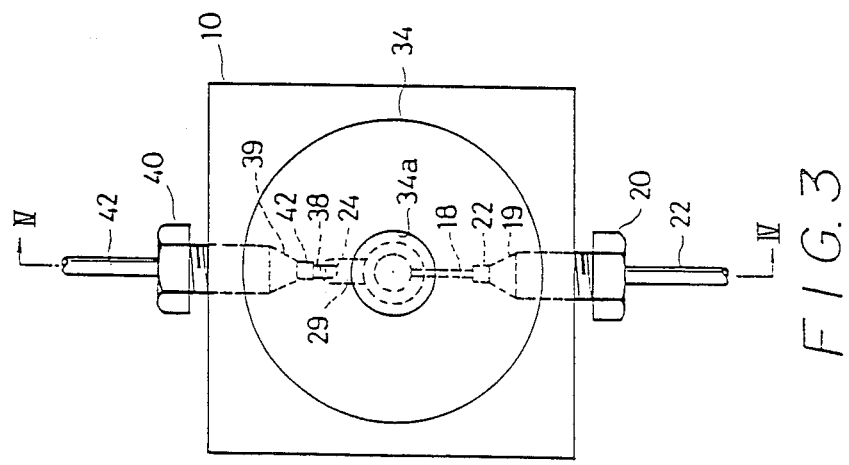
FIG. 3 is a front view of a split stream flow cell of a second embodiment.

A second embodiment of the present invention is described below with reference to FIGS. 3 and 4. FIG. 3 is a front view of a split stream flow cell and FIG. 4 is a sectional view taken along the line IV—IV of FIG. 3.

This split stream flow cell differs from the first embodiment with respect to the shape of a split flow channel 12A thereof, and it does not have the cylindrical portion 13 shown in FIG. 2. The split flow channel 12A comprises truncated cone portions 14A and 16A which each have a diameter increasing toward the end thereof from the center of the split flow channel 12A. The other features are the same as those of the first embodiment.

The split stream flow cell shown in FIGS. 3 and 4 is compared with the conventional tapered cell below, using an example of numerical values of the dimensions thereof.

In the split flow channel 12A, the axial length is 9.4 mm, the inner diameter at the center is 0.7 mm, the diameter of each of the openings at both ends is 1.2 mm, and the inclination of the inner wall of the truncated cone portion 14 with respect to the axis of the split flow channel 12A is 3.0°. The volume of the cell is 9.1 l.

On the other hand, in the tapered cell with which the split stream flow cell is compared, if the diameter of the opening on the small-diameter side is 0.7 mm, the inclination of the inner wall with respect to the axis thereof is 3.0°, and the axial length is 9.4 mm, the volume of the cell is 16.9 l. In other words, the volume of the split stream flow cell is 1/1.9 of the volume of the tapered cell.

Figure 6:
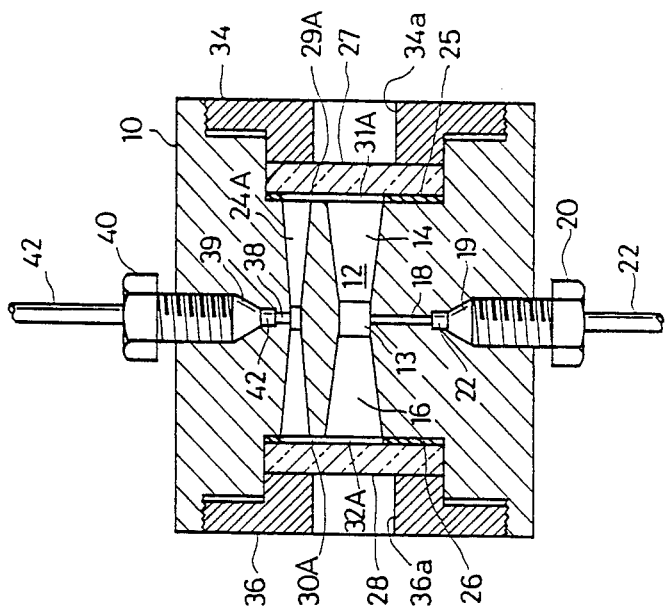
FIG. 6 is a sectional view taken along the line VI—VI of FIG. 5.
Figure 5:
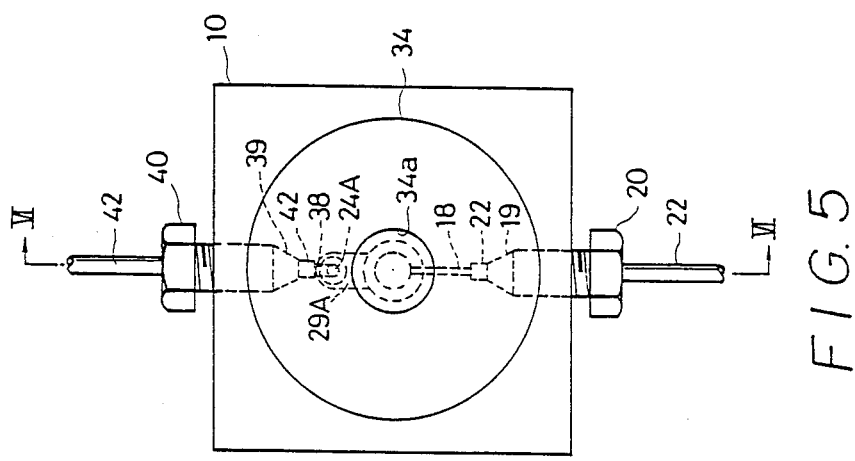
FIG. 5 is a front view of a split flow cell of a third embodiment.

A third embodiment of the present invention is described below with reference to FIGS. 5 and 6. FIG. 5 is a front view of a split stream flow cell, and FIG. 6 is a sectional view taken along the line VI—VI of FIG. 5.

This split stream flow cell differs from the first embodiment with respect to the shape of a confluent channel 24A thereof. The confluent channel 24A comprises a cylindrical portion provided at the center thereof and truncated cone portions which each have a diameter increasing toward the end thereof. The other features are the same as those of the first embodiment.

Although a simple increase in the inner diameter of the confluent channel 24 shown in FIG. 2 does not affect the results of measurements, a tapered confluent channel such as that shown in FIG. 5 causes the level of the base line to be reduced. It is thought that this is caused by an improved symmetry in the flows of the sample solution between the truncated cone portions 14, 16 in the split flow channel 12. In other words, this is because, even if the symmetry of the flows in the truncated cone portions 14, 16 deteriorates, producing a difference in pressures between the two ends of the confluent channel 24A, the difference is reduced at the central portion of the confluent channel 24A, and the symmetry of the flows in the central portion is maintained, whereby the symmetry of the flows in the split flow channel 12 is prevented from further deteriorating. A lack of symmetry of the flows in the split flow channel 12 is changed to a state wherein the symmetry of the flows is maintained because a large amount of sample solution flows from the inlet channel 18 to the split flow channel 12 in the direction in which the sample solution flows easily (in the direction toward a lower pressure).

(Test example)

An example of a test examining the degree of the effect of the split stream flow cell shown in FIGS. 1 and 2 is described below. The values of the dimensions of the split stream flow cell are the same as those of the above-described example.

The dimensions of the tapered cell with which the split stream flow cell is compared are such that the diameter of one end is 1.0 mm, the diameter of the other end is 1.5 mm, and the axial length is 10.0 mm.

Figure 7:
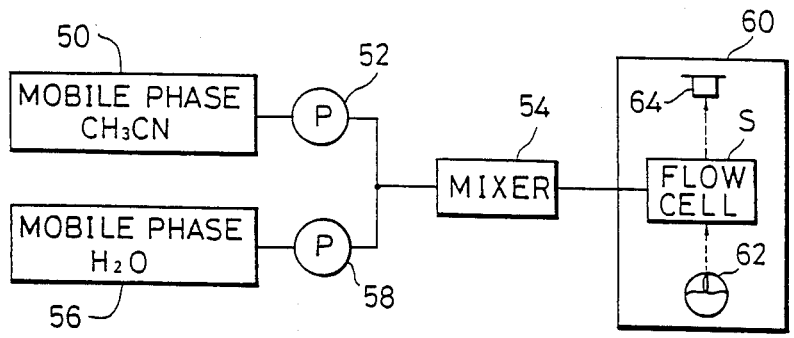
FIGS. 7 to 12 are drawings concerning tests examining the effects of the present invention.

FIG. 7 shows a testing device in which acetonitrile ($CH_3CN$) in a storage tank for a mobile phase 50 is sent to a mixer 54 by means of a pump 52, and the water in a storage tank for a mobile phase 56 is also sent to the mixer 54 by means of a pump 58. The mixing ratio of the two liquids is set by a program in a controller (not shown) which controls the flows of the pumps 52, 58. The mobile phase mixed at high pressure in the mixer 54 is passed through a flow cell S constituting a UV detector 60. A bundle of light rays from a light source 62 is transmitted through the split flow channel 12 of the flow cell S, and the strength of the light transmitted therethrough is detected by a photodetector element 64.

The UV detector 60 has a detection wavelength of 250 mm and sensitivity of 0.04 AUFS (absorbance over a full-scale).

Figure 8:
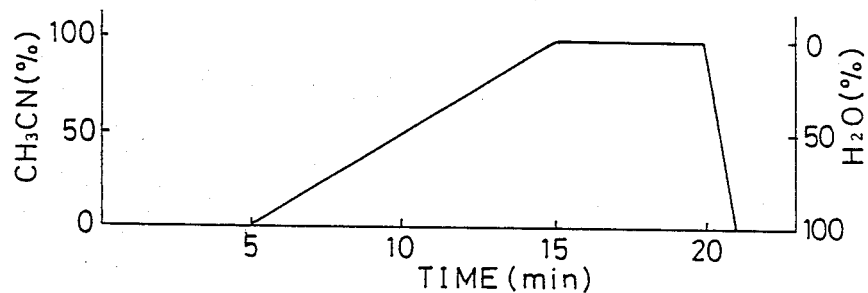
Figure 9:
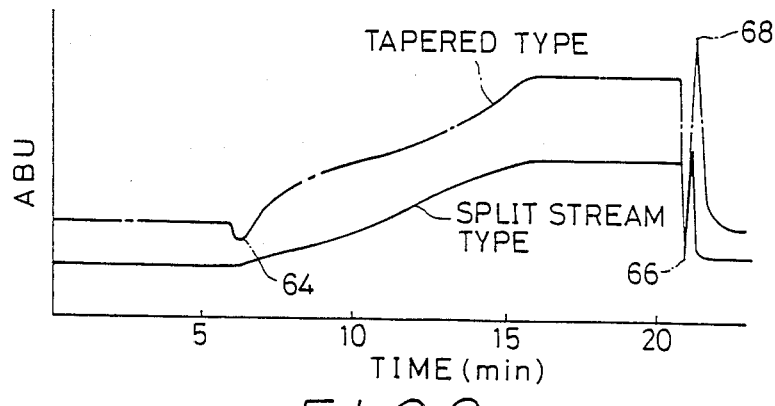

A test of gradient elution is first described below. The mixing ratio of water and acetonitrile was changed as shown in FIG. 8. The total flow was 1.0 ml/min, and the base line of the output from the UV detector 60 varied as shown in FIG. 9. In FIG. 9, the broken line shows the case in which the conventional tapered cell was used, and the solid line shows the case in which the split stream flow cell shown in FIG. 1 was used.

When the tapered cell was used, bottoms 64, 66 and a peak 68 appeared. This was caused by the liquid lens effect produced in the interface between the water and the acetonitrile.

On the other hand, when the split stream flow cell was used, the bottom 64 disappeared, and the bottom 66 and the peak 68 became small.

It is clear from these results that the use of the split stream flow cell greatly reduces the influence of the liquid lens effect.

A description will now be made of a test in which the flow of a mobile phase comprising one component is changed.

Figure 10:
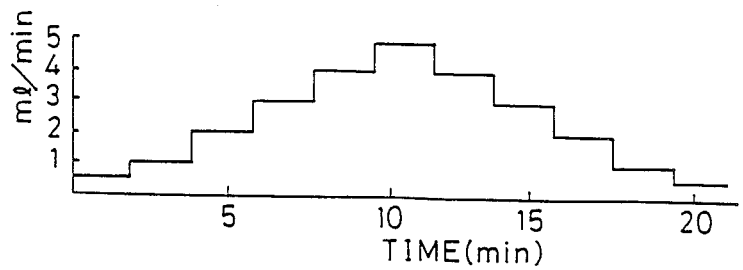
Figure 11:
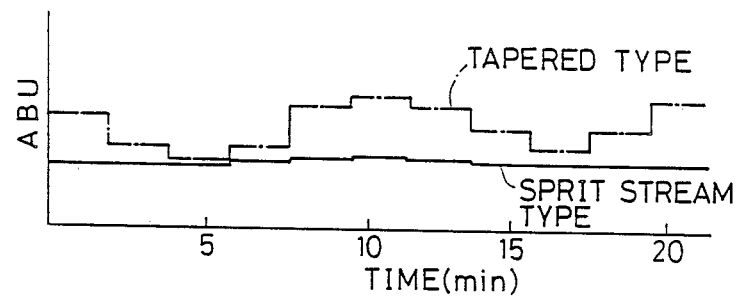

The mobile phase comprised 100% acetonitrile, and the flow of the mobile phase was stepwisely increased from 0.5 ml/min to 5 ml/min, then stepwisely decreased to 0.5 ml/min, as shown in FIG. 10. The sensitivity of the UV detector 60 was set to 0.02 AUFS. In this case, the base line of the output from the UV detector 60 varied as shown in FIG. 11. In FIG. 11, the broken line shows the case in which the conventional tapered cell was used, and the solid line shows the case in which the split stream flow cell shown in FIG. 1 was used.

It is clear from FIG. 11 that the use of the split stream flow cell greatly reduces the influence of the flow effect, when compared with the use of the tapered cell. Therefore, it is possible to perform measurements with a with high degree of sensitivity.

A description will now be made of a test in which the diameter of the inlet channel 18 shown in FIG. 2 is changed.

Figure 12:
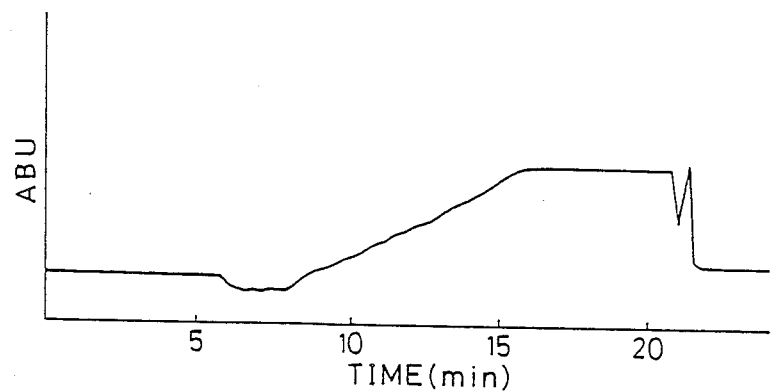

The solid line of FIG. 9 shows the case in which the diameter of the inlet channel 18 was 0.25 mm. It was found that, if the diameter was changed to 0.8 mm, the base line greatly varied, as shown in FIG. 12.

This is because, if the diameter is increased, the rate of the flow from the inlet channel 18 to the split flow channel 12 is reduced, and thus a laminar flow is easily formed in the split flow channel 12, resulting in an increase in the liquid lens effect.

It is preferable that the smaller the ratio of inner diameters of the inlet channel 18 and the center of the split flow channel 12, the longer the axial length of the cylindrical portion 13 and the larger the inner diameter of the cylindrical portion 13.

The above-described embodiments concern the case of a split flow channel having truncated cone portions, but the present invention is not limited to this case. The split flow channel may have a form in which the diameter thereof increases from a given position at its center toward either end, or it may have the form of a body of rotation of a quadratic or cubic curve.

In addition, the split stream flow cell may have the configuration in which the contact surfaces between the block 10 and the window plates 27, 28 are sealed by the windows plates themselves without using the packings 25, 26, and in which the split flow channel and the confluent channel are caused to communicate with each other by forming grooves in the surfaces of the window plates 27, 28 or the block 10 which are opposite to each other. The split stream flow cell may also have the configuration in which no confluent channel 24 is formed and both ends of the split flow channel are caused to communicate with individual outlet channels.

What is claimed is:

1. A split stream flow cell for a UV detector comprising a cell block (10), a split flow channel (12, 12A) passing through said cell block (10), an inlet channel (18) communicating with the center of said split flow channel (12, 12A), an outlet channel (38) communicating with the ends of said split flow channel (12, 12A), and transparent window members which serve to close openings at the ends of said split flow channel, said stream flow cell being characterized in that both sides of said split flow channel (12, 12A) are symmetrical with respect to a central portion (13) and the diameter of thereof is increased from a given position in said central portion (13) toward its ends.

2. A split stream flow cell according to claim 1, wherein the diameter of said split flow channel (12, 12A) is uniform in said central portion (13).

3. A split stream flow cell according to claim 2 further comprising a confluent channel (24) which passes through said cell block (10) and has one end communicating with one end of said split flow channel (12, 12A), the other end communicating with the other end of said split flow channel (12, 12A), and a central portion communicating with said outlet channel (38).

4. A split stream flow cell according to claim 3, wherein both sides of said confluent channel (24) are symmetrical with respect to the center thereof and the axis of said confluent channel (24) is parallel to the axis of said split flow channel (12, 12A).

5. A split stream flow cell according to claim 4, wherein said window members (27, 28) are pressed at both ends of said split flow channel (12, 12A) and said confluent channel (24) through packings (25, 26) having holes (29, 30) which are formed therein and through which said split flow channel (12, 12A) and said confluent channel (24) are caused to communicate with each other.

6. A split stream flow cell according to claim 5, wherein the diameter of said confluent channel (24) is increased from a given position in a central portion toward its ends.

7. A split stream flow cell according to claim 1, wherein the diameter of said split flow channel (12, 12A) is increased from the center thereof toward its ends.

8. A split stream flow cell according to claim 7 further comprising a confluent channel (24) which passes through said cell block (10) and has one end communicating with one end of said split flow channel (12, 12A), the other end communicating with the other end of said split flow channel (12, 12A), and a central portion communicating with said outlet channel (38).

9. A split stream flow cell according to claim 8, wherein both sides of said confluent channel (24) are symmetrical with respect to the center thereof and the axis of said confluent channel (24) is parallel to the axis of said split flow channel (12, 12A).

10. A split stream flow cell according to claim 9, wherein said window members (27, 28) are pressed at both ends of said split flow channel (12, 12A) and said confluent channel (24) through packings (25, 26) having holes (29, 30) which are formed therein and through which said split flow channel (12, 12A) and said confluent channel (24) are caused to communicate with each other.

11. A split stream flow cell according to claim 10, wherein the diameter of said confluent channel (24) is increased from a given position in a central portion toward its ends.

* * * * *